United States Patent [19]

Cretois

[11] Patent Number: 5,558,859
[45] Date of Patent: Sep. 24, 1996

[54] COMPOSITION FOR THE TREATMENT AND PROTECTION OF THE EXOSKELETAL PARTS BASED ON CERAMIDES AND VINYLPYRROLIDONE POLYMERS

[75] Inventor: Isabelle Cretois, Clischy, France

[73] Assignee: L'Oreal, Paris, France

[21] Appl. No.: 433,929

[22] Filed: May 2, 1995

[30] Foreign Application Priority Data

May 2, 1994 [FR] France ................... 94-05314

[51] Int. Cl.$^6$ ................... A61K 7/06; A61K 7/032
[52] U.S. Cl. ................... 424/70.15
[58] Field of Search ................... 424/70.15; 514/772.5

[56] References Cited

FOREIGN PATENT DOCUMENTS

| | | |
|---|---|---|
| WO-A-9302656 | 2/1993 | WIPO. |
| WO-A-9314024 | 7/1993 | WIPO. |
| WO-A-9402115 | 2/1994 | WIPO. |

OTHER PUBLICATIONS

C.A. 166:66924 Spellman et al.

*Primary Examiner*—Peter F. Kulkosky
*Attorney, Agent, or Firm*—Finnegan, Henderson, Farabow, Garrett & Dunner

[57] ABSTRACT

Compositions for the treatment and protection of the exoskeletal parts, in particular the hair and the eyelashes, characterized in that they contain, in a cosmetically acceptable medium, at least one ceramide and/or one glycoceramide and at least one vinylpyrrolidone polymer are disclosed. A process which uses these compositions for the nonwashing treatment of the exoskeletal parts, in particular of the hair and the eyelashes is also disclosed, as is a cosmetic treatment process making use of these compositions.

17 Claims, No Drawings

COMPOSITION FOR THE TREATMENT AND PROTECTION OF THE EXOSKELETAL PARTS BASED ON CERAMIDES AND VINYLPYRROLIDONE POLYMERS

The present invention is directed to compositions intended for the treatment and the protection of keratinous exoskeletal parts, in particular the hair and the eyelashes, which contain, in a cosmetically acceptable medium, at least one ceramide and/or glycoceramide and at least one vinylpyrrolidone polymer.

The invention is also directed to the use of such compositions for a nonwashing treatment of the keratinous exoskeletal parts, in particular of the hair and the eyelashes, and to the cosmetic treatment process making use of such compositions.

Formulations enabling hair and/or eyelashes to be set and conditioned are already known in the state of the art. Vinylpyrrolidone polymers, which have the advantage of maintaining the waviness of hair and/or of eyelashes in high humidity conditions have already been employed for this purpose.

Ceramides and glycoceramides are also known, and have already been combined with cholesterol esters with the aim of protecting the hair fibre. However, ceramides have never been described in relation to imparting good shape-retention to the hair.

However, it has now been discovered, after considerable research, that the combination of ceramides and/or glycoceramides with vinylpyrrolidone polymers results unexpectedly and surprisingly in particularly advantageous properties, especially a remarkable improvement in the shape-retention of the hair style over time. This discovery is the basis of the present invention.

A subject of the present invention is therefore new nonwashing cosmetic compositions for the treatment and the protection of keratinous exoskeletal parts, in particular the hair and the eyelashes, containing, in a nondetergent cosmetically acceptable medium, at least one ceramide and/or glycoceramide and at least one vinylpyrrolidone polymer, the compositions containing less than 4 % of anionic, amphoteric and/or zwitterionic surface-active agents.

Another subject of the invention relates to the use of these compositions for the nonwashing treatment of the keratinous exoskeletal parts, in particular the hair and the eyelashes. It is appropriate here to define a nonwashing treatment as a treatment which makes use of a composition containing less than 4% by weight of anionic, amphoteric and/or zwitterionic surface-active agents. Another subject of the invention also relates to the cosmetic treatment process making use of such compositions.

Other characteristics, aspects, subjects and advantages of the invention will appear still more clearly on reading the description and the examples which follow. Exoskeletal parts include the hair, the eyelashes, the eyebrows, the fingernails or the toenails. Ceramides and/or glycoceramides are known per se and are natural or synthetic molecules which may correspond to formula:

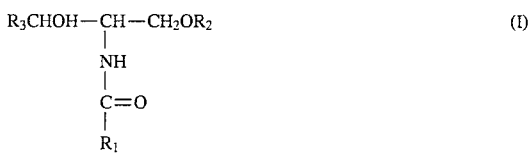

in which:

$R_1$ represents a saturated or unsaturated, linear or branched alkyl radical derived from a $C_{14}$–$C_{30}$ fatty acid, it being possible for this radical to be substituted by a hydroxyl group in its G position, wherein the hydroxyl group is esterified with a saturated or unsaturated $C_{16}$–$C_{30}$ fatty acid, or a hydroxyl group in its ω position, wherein the hydroxyl group is esterified with a saturated or unsaturated $C_{16}$–$C_{30}$ fatty acid;

$R_2$ represents a hydrogen atom or a (glycosyl)$_n$, (galactosyl)$_m$ or sulphogalactosyl radical, in which n is an integer ranging from 1 to 4 and m is an integer ranging from 1 to 8;

$R_3$ represents a saturated or α-unsaturated $C_{15}$–$C_{26}$ hydrocarbon radical, it being possible for this radical to be substituted by one or more $C_1$–$C_{14}$ alkyl radicals, or $R_3$ may represent a $C_{15}$–$C_{26}$ α-hydroxyalkyl radical, wherein the hydroxyl group of the $C_{15}$–$C_{26}$ α-hydroxyalkyl radical may be esterified by a $C_{16}$–$C_{30}$ α-hydroxy acid.

The preferred ceramides within the scope of the present invention are those described by Downing in Arch. Dermatol., Vol. 123, 1381–1384, 1987, or those described in French patent FR-2 673 179, the disclosures of which are incorporated herein by reference, and the structures of which may be the following:

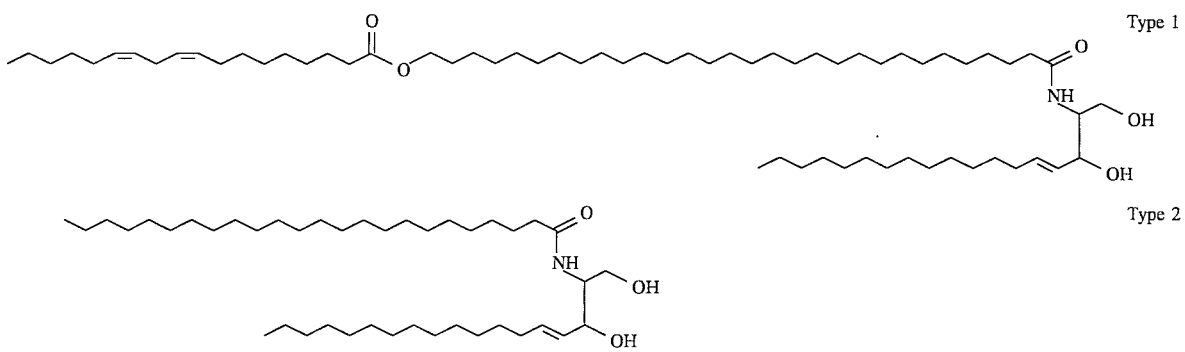

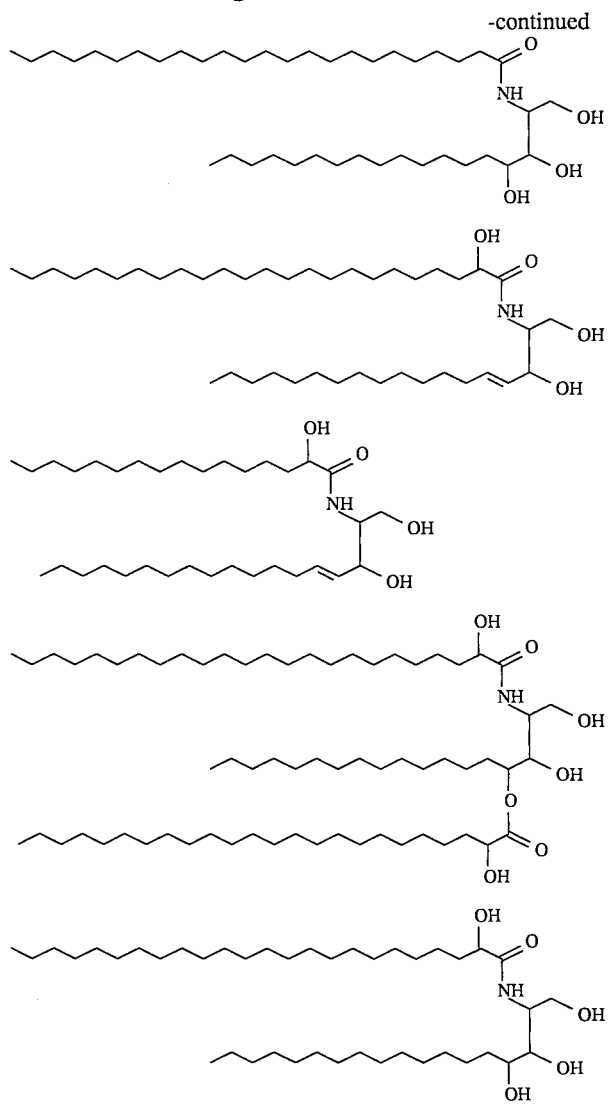

Type 3

Type 4

Type 5

Type 6 I

Type 6 II

The ceramides which are more particularly preferred according to the invention are the compounds of formula (I) in which $R_1$ represents a saturated or unsaturated alkyl derived from a $C_{16}$–$C_{22}$ fatty acid; $R_2$ represents a hydrogen atom; and $R_3$ represents a $C_{15}$ saturated linear radical.

Such compounds are, for example:

N-linoleoyldihydrosphingosine,
N-oleoyldihydrosphingosine,
N-palmitoyldihydrosphingosine,
N-stearoyldihydrosphingosine,
N-behenoyldihydrosphingosine,
or mixtures of these compounds.

Still more preferably, use is made of the compounds of formula (I) in which $R_1$ represents a saturated or unsaturated alkyl radical derived from a fatty acid, $R_2$ represents a galactosyl or sulphogalactosyl radical and $R_3$ represents a —CH=CH—(CH$_2$)$_{12}$—CH$_3$ group.

By way of example the product consisting of a mixture of these compounds and sold under the trade name Glycocer by Waitaki International Biosciences may be mentioned.

The concentration of these ceramides and/or glycoceramides may preferably range approximately from 0.005% and 5% by weight relative to the total weight of the composition, and more preferably approximately from 0.01 to 3%.

The vinylpyrrolidone polymers (PVP) which may be used in accordance with the invention are preferably chosen from the following polymers:

a) vinylpyrrolidone polymers containing dimethylaminoethyl methacrylate units; among these there may preferably be mentioned:

the vinylpyrrolidone/dimethylaminoethyl methacrylate (20/80 by weight) copolymer sold under the trade name Copolymer 845 by I.S.P.;

the vinylpyrrolidone/dimethylaminomethyl methacrylate copolymers quaternized with diethyl sulphate and sold under the names Gafquat 734, 755, 755 S and 755 L by I.S.P.;

the hydrophilic PVP/dimethylaminoethyl methacrylate/polyurethanes sold under the trade name Pecogel GC-310 by U.C.I.B. or under the names Aquamere C 1031 and C 1511 by Blagden Chemicals;

the-quaternized or unquaternized PVP/dimethylaminoethyl methacrylate/$C_8$–$C_{16}$ olefins sold under the names Ganex ACP 1050 to 1057, 1062 to 1069, 1079 to 1086 by I.S.P.; and the PVP/dimethylaminoethyl methacrylate/vinylcaprolactam sold under the name Gaffix VC 713 by I.S.P.;

b) vinylpyrrolidone polymers containing methacrylamidopropyltrimethylammonium (M.A.P.T.A.C.) units, among which it is possible to particularly mention:
the vinylpyrrolidone/M.A.P.T.A.C. copolymers sold under the trade names Gafquat ACP 1011 and Gafquat HS 100 by I.S.P.; and
the vinylpyrrolidone/M.A.P.T.A.C./ vinylcaprolactam terpolymers sold under the names Polymer ACP 1059, 1060 and 1156 by I.S.P.;
c) vinylpyrrolidone polymers containing methylvinylimidazolium units, and among which it is possible to mention more particularly:
PVP/methylvinylimidazolium chlorides sold under the names Luviquat FC 370, FC 550, FC 905, HM 552 by B.A.S.F.;
the PVP/methylvinylimidazolium chloride/vinylimidazole sold under the name Luviquat 8155 by B.A.S.F.; and
the PVP/methylvinylimidazolium methosulphate sold under the name Luviquat MS 370 by B.A.S.F.

The concentration of these vinylpyrrolidone polymers may preferably range approximately from 0.05 to 5% by weight relative to the total weight of the composition, and more preferably approximately from 0.1 to 3%.

The anionic and amphoteric and/or zwitterionic surface-active agents are chosen from surface-active agents having detergent properties. They are used in proportions which are sufficient to impart detergent properties to the composition, i.e., "detergent proportions".

Among the anionic surface-active agents which may be mentioned are the alkali metal salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkylsulphonates, alkylamide sulphonates, alkylarylsulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates, and N-acyltaurates.

The alkyl or acyl radical of these various compounds generally consists of a carbon chain containing from 12 to 20 carbon atoms. The aryl radical generally consists of a phenyl or benzyl group.

Among the anionic surface-active agents which may also be mentioned are fatty acid salts such as the salts of oleic acid, ricinoleic acid, palmitic acid and stearic acid; coconut oil acid and hydrogenated coconut oil acid; acyl lactylates, the acyl radical of which contains from 8 to 20 carbon atoms.

It is also possible to use surface-active agents which are generally classified in the family of weakly anionic agents such as alkyl-D-galactosiduronic acids and salts thereof and polyoxyalkylenated carboxylic ether acids and salts thereof, and in particular those containing 2 to 50 ethylene oxide groups.

There may more particularly be mentioned the polyoxyethylenated carboxylic ether acids and acid salts of formula:

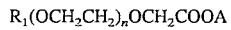

$R_1(OCH_2CH_2)_nOCH_2COOA$ in which $R_1$ is an alkyl or alkaryl radical and n has an average value from 2 to 20, the alkyl radical having from 6 to 20 carbon atoms, aryl preferably denoting phenyl, and A denoting hydrogen, an alkali metal or an alkaline-earth metal, an amine or an ammonium.

There may more particularly be mentioned the products sold under the name AKYPO by the company CHEM'Y.

The amphoteric and/or zwitterionic surface-active agents are preferably chosen from aliphatic secondary or tertiary amine derivatives in which the aliphatic radical is a straight or branched chain containing 8 to 18 carbon atoms and containing at least one water-soluble anionic group such as carboxylate, sulphonates, sulphate, phosphate or phosphonate.

Alkyl ($C_8$–$C_{20}$)betaines, sulphobetaines, alkyl ($C_8$–$C_{20}$) amidoalkyl ($C_1$–$C_6$)betaines and alkyl ($C_8$–$C_{20}$) amidoalkyl($C_1$–$C_6$)sulphobetaines may also be mentioned.

Among the amine derivatives which may be mentioned are the products sold under the name MIRANOL, such as those described in U.S. Pat. Nos. 2,528,378 and 2,781,354, the disclosures of which are hereby incorporated by reference, and classified in the CTFA Dictionary, 5th edition, 1993, under the names "Disodium cocoamphodiacetate" and "Disodium amphocarboxypropionate".

The cosmetically acceptable medium preferably consists of water or a mixture of water and cosmetically acceptable solvents such as monoalcohols, polyalcohols, glycol ethers or fatty acid esters, which may be employed alone or as a mixture.

More particular mention may be made of lower alcohols such as ethanol, isopropanol, polyalcohols such as diethylene glycol, glycol ethers and glycol or diethylene glycol alkyl ethers.

The pH of the compositions according to the invention preferably ranges from 2 to 9 and more preferably ranges from 3 to 8. The pH may be adjusted to the chosen value by means of alkalilying or acidifying agents usually used in cosmetics for this type of application.

These compositions may additionally contain surface-active agents of nonionic and/or cationic type, which are well known in the state of the art, this being in proportions which preferably range from approximately 0.1 to 10% by weight relative to the whole composition.

In addition to the ceramides and/or glycoceramides and the vinylpyrrolidone polymers defined above, the compositions according to the invention may further contain thickening agents, preserving agents, sequestrants, softeners, perfumes, colorants, viscosity modifiers, foam modifiers, foaming agents, foam stabilizers, pearlescent agents, hydrating agents, antidandruff agents, antiseborrhoeic agents, sunscreens, proteins, vitamins, plasticizers, α-hydroxyacids, electrolytes, propellant and perfumes.

The compositions according to the invention may also contain other conditioning agents. These conditioning agents may be chosen from natural or synthetic oils and waxes, fatty alcohols, esters of polyhydric alcohols, glycerides, silicone gums and resins or mixtures of these various compounds.

The compositions employed according to the invention are, for example, rinsed or unrinsed hair-care compositions and compositions for making-up the eyelashes or the eyebrows, such as mascaras.

The compositions according to the invention may be applied before or after shampooing, dyeing, bleaching or permanent waving or may be applied between the reduction and fixing stages of a permanent waving or a straightening operation.

The compositions applied to the keratinous exoskeletal parts may be in various forms, such as in the form of emulsions, dispersions, solutions, more or less thickened fluids, gels, creams and gel-creams.

They may be employed as they are or may be diluted before use.

In particular, they may be packaged under pressure in an aerosol bottle in the presence of a propellant and form a mousse, or in a pump bottle, in order to be delivered in the form of a spray.

The nonwashing process for the treatment and protection of the keratinous exoskeletal parts is characterized in that a composition containing at least one ceramide and/or one glycoceramide and at least one vinylpyrrolidone polymer is applied to the exoskeletal parts, in particular the hair and the eyelashes and that, after an optional exposure time, rinsing is optionally carried out.

Concrete examples illustrating the invention will now be given.

EXAMPLE 1

A hair styling mousse of the following composition was prepared:

| | |
|---|---|
| Hydroxyethyl cellulose modified with a cetyl chain, sold under the name Natrosol Plus Grade 330 CS by Aqualon | 0.1 g |
| Copolymer of vinylpyrrolidone and of dimethylaminoethyl methacrylate, quaternized with diethylsulphate, sold in solution at a concentration of 50% in ethanol by I.S.F. under the name Gafquat 734 | 0.75 g AS |
| Butanediol oxypropylenated with 10 moles of propylene oxide, sold under the name of Macol 57 by Mazer | 0.5 g |
| Cetyl dimethyl (2-hydroxyethyl) ammonium phosphate in aqueous solution at a concentration of 30% | 0.15 g AS |
| Octylphenol containing 10 moles of ethylene oxide, sold under the name of Igepal O by Rhône Poulenc | 0.3 g |
| Polyvinyl alcohol sold under the name of Covol 9740 by C.P.C. Int | 0.6 g |
| N-Oleoyldihydrosphingosine | 0.1 g |
| 1-Methyl-2-tallow-3-tallowamidoethylimidazolinium methosulphate at a concentration of 75% in propylene glycol | 0.375 g |
| Stabilizer | q.s. |
| Perfume | q.s. |
| Demineralized water | q.s. 100 g |

Packaging as aerosol:

90 g of the above composition were packaged in an aerosol container in the presence of 10 g of a ternary mixture of n-butane, isobutane and propane (23/55/22), sold under the name "Aerogaz 3,2N by Elf Aquitaine.

This mousse was applied to wet hair and, after drying of the latter, gave the hair good shape-retention over time.

EXAMPLE 2

A hair styling mousse of the following composition was prepared:

| | |
|---|---|
| Nonoxynyl hydroxyethyl cellulose sold under the name Amercell Polymer HM 1500 by Amerchol | 0.1 g |
| Copolymer of vinylpyrrolidone and of methylvinylimidazolium chloride (70/30), sold in aqueous solution at a concentration of 40% by B.A.S.F. under the name Luviquat FC 370 | 0.2 g AS |
| Hydrogenated castor oil oxyethylenated with 40 moles of ethylene oxide, sold under the name Cremophor RH 40 by B.A.S.F | 0.25 g |
| Butanediol oxypropylenated with 10 moles of propylene oxide, sold under the name of Macol 57 by Mazer | 0.4 g |
| Octylphenol containing 10 moles of ethylene oxide, sold under the name of Igepal O by Rhône Poulenc | 0.4 g |
| Polyvinyl alcohol sold under the name of Covol 9740 by C.P.C. Int | 0.8 g |
| N-Oleoyldihydrosphingosine | 0.05 g |
| Stabilizer | q.s. |
| Perfume | q.s. |
| Demineralized water | q.s. 100 g |

Packaging as aerosol: 90 g of the above composition were packaged in an aerosol container in the presence of 10 g of a ternary mixture of n-butane, isobutane and propane (23/55/22), sold under the name of "Aerogaz 3,2 N by Elf Aquitaine.

This mousse was applied to wet hair and, after drying of the hair, gave the hair good shape-retention over time.

EXAMPLE 3

A hair-setting lotion (A) according to the invention, of the following composition, was prepared:

| | |
|---|---|
| Copolymer of vinylpyrrolidone and of methylvinylimidazolium chloride (70/30), sold in aqueous solution at a concentration of 40% by B.A.S.F. under the name Luviquat FC 370 | 0.5 g AS |
| N-Oleoyldihydrosphingosine | 0.05 g |
| 1-Methyl-2-tallow-3-tallowamidoethyl-imidazolinium methosulphate at a concentration of 75% in propylene glycol (Rewoquat W 75 PG from REWO) | 0.5 g AS |
| Demineralized water | q.s. 100 g |
| A hair-setting lotion (B) not in accordance with the invention (i.e., lotion (A) without ceramide), of the following composition, was prepared: | |
| Copolymer of vinylpyrrolidone and of methylvinylimidazolium chloride (70/30), sold in aqueous solution at a concentration of 40% by B.A.S.F. under the name Luviquat FC 370 | 0.5 g AS |
| 1-Methyl-2-tallow-3-tallowamidoethyl-imidazolinium methosulphate at a concentration of 75% in propylene glycol (Rewoquat W 75 PG from Rewo) | 0.5 g AS |
| Demineralized water | q.s. 100 g |

The operating method was the following: either lotion (A) or lotion (B) was applied to locks of hair. The locks thus treated were then wound onto rollers. The lock was then dried and finally the lock was unwound from the roller.

To quantify the effectiveness of the composition according to the invention, the initial length $L_0$ (in cm) of the lock of hair was first measured before the steam treatment (length measured between the roots and the tips on a lock suspended vertically); the length $L_1$ of this same lock just at the end of treatment was then measured in the same way; and, finally, the length $L_2$ of this lock was measured 5 hours after the treatment.

The shape retention (in %) of the set is defined by the ratio $$\frac{L_n - L_2}{L_0 - L_1} \times 100$$

The higher this ratio is, the better the set will be.

The results obtained were the following:

For the lotion (A) according to the invention, the shape-retention of the set was 48.3%, whereas for the lotion (B) it was 43.5%; i.e. an increase of more than was achieved with the lotion (A).

EXAMPLE 4

A mascara, in accordance with the invention, of the following composition was prepared:

| Phase A: | |
| --- | --- |
| Beeswax | 6.9 g |
| Carnauba wax | 4.16 g |
| Paraffin | 11.4 g |
| Stearic acid | 7.7 g |
| N-oleyl dihydrosphingosine | 0.2 g |
| Phase B: | |
| Black iron oxide | 5.55 g |
| Phase C: | |
| Polyvinylpyrrolidone (POVIDONE USP from ISP) | 0.5 g |
| Triethanolamine | 3.8 g |
| Arabic gum | 4.5 g |
| Hydroxyethylcellulose | 0.16 g |
| preserving agents q.s. | |
| deminieralized wager q.s. | 100 g |

Phase A was melted at 80° C. and phase B was then introduced and was dispersed using a homogenizer for 30 minutes.

Phase C was prepared by introducing the first three components of this phase into water maintained at 75° C.

An emulsion was then produced by mixing phase C into phase A+B.

The mascara composition was applied to the eyelashes. The eyelashes were observed to exhibit good hold.

What is claimed is:

1. A composition for improving the shape-retention of hair, eyelashes or eyebrows, which comprises, in a cosmetically acceptable medium, at least one compound selected from a ceramide and a gtycoceramide and at least one vinylpyrrolidone polymer, said at least one compound and said at least one vinylpyrrolidone polymer being present in said composition in an amount effective to improve the shape-retention of said hair, eyelashes or eyebrows, said composition containing less than 4% by weight of anionic and/or amphotetric and/or zwitterionic surface-active agents.

2. The composition according to claim 1, wherein said at least one compound selected from a ceramide and a glycoceramide is selected from compounds of formula (I):

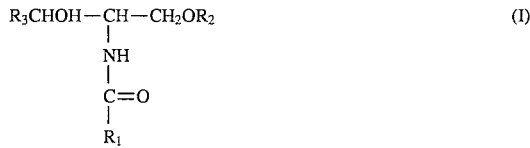

in which:

$R_1$ represents a saturated or unsaturated, linear or branched alkyl radical derived from a $C_{14}$–$C_{30}$ fatty acid, it being possible for said radical to be substituted by a hydroxyl group in its α position, wherein the hydroxyl group is esterified with a saturated or unsaturated $C_{16}$–$C_{30}$ fatty acid, or a hydroxyl group in its ω position, wherein the hydroxyl group is esterified with a saturated or unsaturated $C_{16}$–$C_{30}$ fatty acid;

$R_2$ represents a hydrogen atom or a (glycosyl)$_n$, (galactosyl)$_m$ or sulphogalactosyl radical, in which n is an integer ranging from 1 to 4 and m is an integer ranging from 1 to 8;

$R_3$ represents a saturated or α-unsaturated $C_{15}$–$C_{26}$ hydrocarbon radical, it being possible for said radical to be substituted by one or more $C_1$–$C_{14}$ alkyl radicals, or $R_3$ may represent a $C_{15}$–$C_{26}$ α-hydroxyalkyl radical, wherein the hydroxyl group of said $C_{15}$–$C_{26}$ α-hydroxyalkyl radical may be esterified by a $C_{16}$–$C_{30}$ α-hydroxy acid.

3. The composition according to claim 1, wherein said at least one vinylpyrrolidone polymer is selected from:

a) vinylpyrrolidone polymers containing dimethylaminoethyl methacrylate units, which may be quaternized;

b) vinylpyrrolidone polymers containing methacrylamidopropyltrimethylammonium units; and c) vinylpyrrolidone polymers containing methylvinylimidazolium units.

4. The composition according to claim 1, wherein said at least one compound selected from a ceramide and a glycoceramide is present in a proportion which ranges from 0.005% to 5% by weight relative to the total weight of the composition.

5. The composition according to claim 4, wherein said at least one compound selected from a ceramide and a glycoceramide is present in a proportion which ranges from 0.01% to 3% by weight relative to the total weight of the composition.

6. The composition according to claim 1, wherein said at least one vinylpyrrolidone polymer is present in a proportion which ranges from 0.05 to 5% by weight relative to the total weight of the composition.

7. The composition according to claim 6, wherein said at least one the vinylpyrrolidone polymer is present in a proportion which ranges from 0.01 to 3% by weight relative to the total weight of the composition.

8. The composition according to claim 1, wherein said cosmetically acceptable medium comprises at least one component selected from water and a cosmetically acceptable solvent, and further wherein said at least one cosmetically acceptable solvent is selected from monoalcohols, polyalcohols, glycol ethers, and fatty acid esters.

9. The composition according to claim 1, which further comprises at least one cosmetically acceptable conditioning agent selected from nonionic and/or cationic surface active agents, thickening agents, preserving agents, sequestrants, softeners, perfumes, colorants, viscosity modifiers, foam modifiers, foaming agents, foam stabilizers, pearlescent agents, hydrating agents, antidandruff agents, antiseborrhoeic agents, sunscreens, proteins, vitamins, plasticizers, α-hydroxyacids, electrolytes, propellants, perfumes and other conditioning agents.

10. The composition according to claim 1, which is in the form of a more or less thickened fluid, a gel, a cream, a gel-cream, a spray or a mousse.

11. The composition according to claim 2, wherein in said at least one compound of formula (I), $R_1$ represents a saturated or unsaturated alkyl derived from a $C_{16}$–$C_{22}$ fatty acid, $R_2$ represents a hydrogen atom and $R_3$ represents a $C_{15}$ saturated linear radical.

12. The composition according to claim 11, wherein said at least one compound of formula (I) is selected from N-linoleoyldihydrosphinogosine, N-oleoyldihydrosphinogosine, N-palmitoyldihydrosphingosine, N-stearoyldihydrosphingosine, and N-behenoyldihydrosphingosine.

13. The composition according to claim 2, wherein in said at least one compound of formula (I), $R_1$ represents a saturated or unsaturated alkyl radical derived from a fatty acid, $R_2$ represents a galactosyl or sulphogalactosyl radical and $R_3$ represents a —CH=CH—(CH$_2$)$_{12}$—CH$_3$ group.

14. A nonwashing process for improving the shape-retention of hair, eyelashes or eyebrows, which comprises the step of applying to said hair, eyelashes or eyebrows a composition for improving the shape-retention of said hair, eyelashes or eyebrows, said composition comprising, in a cosmetically acceptable medium, at least one compound selected from a ceramide and a glycoceramide and at least one vinylpyrrolidone polymer, said at least one compound and said at least one vinylpyrrolidone polymer being present in said composition in an amount effective to improve the shape-retention of said hair, eyelashes or eyebrows, said composition containing less than 4% by weight of anionic and/or amphoteric and/or zwitterionic surface-active agents.

15. The process according to claim 14, wherein following said application of said composition, a rinsing of said hair, eyelashes or eyebrows is carried out.

16. The process according to claim 15, wherein subsequent to said application of said composition and prior to said rinsing, said hair eyelashes or eyebrows are allowed to rest.

17. A process for improving the shape-retention of hair, eyelashes or eyebrows, which comprises applying a composition to said hair, eyelashes eyebrows, for the purpose of improving the shape-retention of said hair, eyelashes or eyebrows, said composition containing, in a cosmetically acceptable medium, at least one compound selected from a ceramide and a glycoceramide and at least one vinylpyrrolidone polymer, said at least one compound and said at least one vinylpyrrolidone polymer being present in said composition in amount effective to improve the shape-retention of said hair, eyelashes or eyebrows, said composition containing less than 4% by weight of anionic, and/or amphoteric and/or zwitterionic surface-active agents.

* * * * *

UNITED STATES PATENT AND TRADEMARK OFFICE
CERTIFICATE OF CORRECTION

PATENT NO. : 5,558,859
DATED : September 24, 1996
INVENTOR(S) : Isabelle CRETOIS It is certified that error appears in the above-indentified patent and that said Letters Patent is hereby corrected as shown below:

Title page, item [75], after "Inventor: Isabelle Cretois", "Clischy" should read --Clichy--.

Claim 1, col. 9, line 36, "gtycoceramide" should read --glycoceramide--.

Claim 2, col. 9, line 57, "a position" should read --α position--.

Claim 16, col. 12, line 1, "hair eyelashes" should read --hair, eyelashes--.

Claim 17, col. 12, line 5, "eyelashes eyebrows" should read --eyelashes or eyebrows--.

Signed and Sealed this

Twenty-first Day of January, 1997

Attest:

BRUCE LEHMAN

*Attesting Officer*     *Commissioner of Patents and Trademarks*